United States Patent
Lindvall

(10) Patent No.: US 11,915,828 B2
(45) Date of Patent: Feb. 27, 2024

(54) SYSTEM AND METHOD OF USING MACHINE LEARNING FOR EXTRACTION OF SYMPTOMS FROM ELECTRONIC HEALTH RECORDS

(71) Applicant: DANA-FARBER CANCER INSTITUTE, INC., Boston, MA (US)

(72) Inventor: Charlotta Lindvall, Chestnut Hill, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 716 days.

(21) Appl. No.: 16/891,305

(22) Filed: Jun. 3, 2020

(65) Prior Publication Data
US 2020/0388396 A1   Dec. 10, 2020

Related U.S. Application Data

(60) Provisional application No. 62/856,832, filed on Jun. 4, 2019.

(51) Int. Cl.
*G16H 50/20* (2018.01)
*G06F 40/295* (2020.01)
*G16H 20/00* (2018.01)
*G16H 10/60* (2018.01)
*G16H 70/60* (2018.01)
*G16H 50/30* (2018.01)

(52) U.S. Cl.
CPC ........... *G16H 50/20* (2018.01); *G06F 40/295* (2020.01); *G16H 10/60* (2018.01); *G16H 20/00* (2018.01); *G16H 50/30* (2018.01); *G16H 70/60* (2018.01)

(58) Field of Classification Search
CPC ........ G16H 50/20; G16H 10/60; G16H 20/00; G16H 50/30; G16H 70/60; G16H 15/00; G06F 40/295; G06F 40/30; G06F 40/279
USPC .......................................................... 704/9
See application file for complete search history.

(56) References Cited

U.S. PATENT DOCUMENTS

| | | | |
|---|---|---|---|
| 10,552,931 B2 | 2/2020 | Sheffer et al. | |
| 10,553,308 B2 | 2/2020 | Baldwin | |
| 2017/0004184 A1* | 1/2017 | Jain | G06F 16/35 |
| 2017/0358295 A1* | 12/2017 | Roux | G06N 5/04 |
| 2018/0314960 A1* | 11/2018 | Martinez Hernandez Magro | G16H 50/20 |

(Continued)

OTHER PUBLICATIONS

Forsyth, Alexander W., et al., Machine Learning Methods to Extract Documentation of Breast Cancer Symptoms from Electronic Health Records, Journal of Pain and Symptom Management, vol. 55, No. 6, Jun. 6, 2018.

*Primary Examiner* — Joy Chng
(74) *Attorney, Agent, or Firm* — BURNS & LEVINSON, LLP; Daniel W. Clarke; Bruce D. Jobse

(57) ABSTRACT

A method for autonomously identifying symptom terms in free running text data includes the acts of defining a plurality of symptom terms associated with a particular pathology or therapeutic substance or procedure, labeling in a text data set any defined symptom terms and associating a tag indicating any of a positive, negative, or other status with relation to the labeled symptom term, and processing with a natural language processing algorithm multiple different subsets of the text data containing labeled symptom terms to identify a frequency of occurrence of a symptom term and to improve identification accuracy.

20 Claims, 9 Drawing Sheets

(56) References Cited

U.S. PATENT DOCUMENTS

2020/0185102 A1\* 6/2020 Leventhal ................ G06N 5/04
2021/0334462 A1\* 10/2021 Kukreja ................ G06F 40/295

\* cited by examiner

```
0.json          1.json    ×

1.json          ▼ root: {} 3 keys
                  ▼ completions: [] 1 item
10.json               ▼ 0: {} 3 keys
                          id: 1001
100.json                  lead_time: 461.301
                        ▼ result: [] 10 items
1000.json                 ▼ 0: {} 6 keys
                              from_name: "Pain"
1004.json                     id: "XDQQhuKAa7"
                              source: "$RPT_TEXT"
101.json                      to_name: "text"
                              type: "labels"
1010.json                   ▼ value: {} 4 keys
                                end: 361
1014.json                     ▼ labels: [] 1 item
                                  0: "General_pain"
1015.json                       start: 357
                                text: ""
1017.json                 ▼ 1: {} 6 keys
                              from_name: "Attributes"
102.json                      id: "ZfznzNCT_t"
                              source: "$RPT_TEXT"
1022.json                     to_name: "text"
                              type: "labels"
1023.json                   ▼ value: {} 4 keys
                                end: 404
1024.json                     ▼ labels: [] 1 item
                                  0: "negation"
1025.json                       start: 402
                                text: ""
1026.json 1028.json 103.json 1034.json 1038.json 104.json 1049.json 105.json
```

| | |
|---|---|
| Human | she denies fever chills but has *rigors* |
| Machine | she denies fever chills but has rigors |
| | |
| Human | ct dye caused a high *fever* and she has a *rash and blistering* |
| Machine | ct dye caused a high *fever* and she has a rash and *blistering* |
| | |
| Human | she also endorses a *chest heaviness* that is related to the *cough* |
| Machine | she also endorses a chest heaviness that is related to the *cough* |
| | |
| Human | no h o diarrhea thus cdi unlikely |
| Machine | no h o diarrhea thus cdi unlikely |
| | |
| Human | she also notes that she has *not eaten all day* |
| Machine | she also notes that she has not eaten all day |
| | |
| Human | she has a *cough* with green sputum and *dysuria* |
| Machine | she has a *cough* with green sputum and dysuria |
| | |
| Human | her pain was well controlled with po pain medications |
| Machine | her *pain* was well controlled with po pain medications |

Negative-labeled words are blue and bolded; positive-labeled words are *red and italicized*.

SYSTEM AND METHOD OF USING MACHINE LEARNING FOR EXTRACTION OF SYMPTOMS FROM ELECTRONIC HEALTH RECORDS

RELATED APPLICATIONS

This application claims the benefit of priority under 35 U.S.C. § 119(e) to U.S. Provisional Application No. 62/856,832, filed Jun. 4, 2019, which is incorporated herein by reference in its entirety.

BACKGROUND OF THE INVENTION

Clinicians document patients' symptoms in free-text format within the electronic health records (EHR). Although symptoms are critically important to quality of life and often provide insight on clinical status changes, computational methods to assess the trajectory of symptoms over time do not currently exist in the clinical setting.

Symptom information derived from electronic health records is currently be extracted utilizing manual chart review, which is time consuming and suffers from ambiguity in the assessment of what is, or is not, a symptom as such. Symptoms can be misidentified as a result of not being perceived as clinical in nature, or can be misidentified linguistically due to the incomplete reading of negating terms within the grammatical structure of the phrase which describes symptoms, or the lack thereof.

For example, patients with cancer commonly experience debilitating symptoms because of the disease, its treatment, or a combination of both. Currently, symptoms are documented primarily as free-text descriptions within clinical notes in the electronic health record. Obtaining a concise overview of patients' symptoms is challenging, which hinders clinical care, quality improvement, and research efforts. Patients accrue tens to hundreds of clinical notes during their treatment course, rendering manual review of every chart costly, error-prone, and infeasible (Matt et al., (2013), J Educ Eval Health Prof.10, 12). Therefore, many research studies do not include symptom variables and, instead, rely on more easily accessible data such as billing codes and laboratory values. Improved access to symptom data would dramatically strengthen the patient-centeredness of outcomes research and clinical care.

Accordingly, a need exists for a system and method in which symptom information can be accurately extracted from patient electronic health records documented in free-text clinical notes.

Further need exists for a system and method in which symptom information can be accurately extracted from patient electronic health records at speeds exceeding that which would be possible for a human.

SUMMARY OF THE INVENTION

Disclosed is a system and technique in which computer executable application can extract symptom information from patient electronic health records at speeds exceeding that which would be possible for a human. Specifically, disclosed is a technique for the development and application of computational algorithms capable of extracting patient-reported symptoms documented within the free-text of electronic health records. Precise definitions of what comprises symptoms are developed utilizing "coding rules" and labeling of term describing symptoms in free-text notes. The generation of these coding rules facilitates the development of machine learning models which can then be employed in the abstraction of various symptomatic concepts contained within free-text notes documented by clinicians.

An executable machine learning model can then be utilized on a large volume of free-text notes documented in electronic health records. More specifically, the disclosed techniques allows for the computer system to generate rules which associate particular sequences of words or characters with a pre-specified symptomatic concept, while other sequences of words have no such association generated, and others may have a negative association with the symptom. This technique facilitates an adaptive machine learning process which occurs as a result of the machine generating a mathematical symptom extraction method which mimics how humans initially abstracted the same symptom information from text-based data storage formats when the first symptom "code book" was created and employed for system extraction.

Through the use of these algorithms, a computer can extract symptom information from patient electronic health records at speeds exceeding that which would be possible for a human. Though free-written text was used as a proof-of-concept, these methods are not limited to purely text-based data and can be expanded to utilize other data sources.

More specifically, a process for derivation of a text data set and a machine model, and training and testing the same, is disclosed. In the first phase of the process, one or more sets of text data are derived from specially chosen progress notes which are then preprocessed by cleaning and segmenting the text and manually annotating, with labels and attributes, possible symptom terms. In the next phase, a large portion of the preprocessed text data set is processed using one or more NLP modeling tools to extract labeled symptom terms within the text data set. The results of the extraction process are measure according to multiple parameters. In the next phase, another smaller portion of the preprocessed text data set with less common labels is processed using the same NLP modeling tool for hyperparameter optimization of the model. In the last phase, the optimized NLP modeling tool is used to extract labeled symptom terms from an as yet tested portion of the text data set. The final extraction process performance is used to determine the frequency of various symptom terms and may be optionally compared with the gold-standard manual chart review.

According to one aspect of the disclosure, a method for identifying symptom in text data comprises: A) defining a plurality of symptom terms; B) selecting a text data set including at least a subset of the plurality of defined symptom terms; C) labeling, in the text data set, defined symptom terms and associating a tag indicating any of a positive, negative, or other status with the labeled symptom term; D) processing, with multiple natural language processing algorithms, a first subset of the text data set containing labeled symptom terms to identify a frequency of occurrences of a symptom term in the first subset of the text data; E) scoring accuracy of the multiple natural language processing algorithms in processing the first subset of the text data; and F) processing, with a natural language processing algorithm having greatest accuracy in step E), a second subset of the text data set containing labeled symptom terms.

According to another aspect of the disclosure, a method for identifying symptom in text data comprises: A) defining a plurality of symptom terms; B) selecting a text data set including at least a subset of the plurality of defined symptom terms; C) labeling, in the text data set, defined symptom terms and associating a position of the labeled symptom term within the text data set and further associating a tag indicating any of a positive, negative, or other status with the labeled symptom term; D) processing, with multiple natural language processing algorithms, a first subset of the text data set containing labeled symptom terms to identify a frequency of occurrences of a symptom term in the first subset of the text data; E) scoring accuracy of the multiple natural language processing algorithms in processing the first subset of the text data; and F) processing, with a natural language processing algorithm having greatest accuracy in step E), a second subset of the text data set containing labeled symptom terms.

According to another aspect of the disclosure, a method for identifying possible toxicities and a therapeutic substance or therapeutic process comprises: A) identifying in a free running text at least one of a plurality of predefined terms describing a symptom of a subject, associating a label with the identified symptom term; B) associating a tag with the labeled symptom term indicating any of a positive, negative, or other status with the labeled symptom term; C) preprocessing the free running text containing labeled terms and other terms with associated attributes into a format readable by a natural language processing algorithm; D) processing, with the natural language processing algorithm, the preprocessed free running text containing labeled terms and terms with associated attributes; and E) processing, with the natural language processing algorithm, other free running text not containing labeled terms or terms with associated attributes.

BRIEF DESCRIPTION OF THE DRAWINGS

The foregoing and other objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

FIG. 5 illustrates conceptually an illustrative output file of the data set of FIG. 4 before extraction in accordance with the disclosure;

FIG. 6 illustrates a side by side comparison symptom terms in text as extracted automatically and manually;

FIG. 7 illustrates examples of sentences with words labeled as symptoms by the human coder as compared to a CRF model analysis in accordance with Example 1 of the disclosure;

DETAILED DESCRIPTION

The present disclosure will be more completely understood through the following description, which should be read in conjunction with the drawings. In this description, like numbers refer to similar elements within various embodiments of the present disclosure. The skilled artisan will readily appreciate that the methods, apparatus and systems described herein are merely exemplary and that variations can be made without departing from the spirit and scope of the disclosure.

The emergence of omnipresent EHRs and powerful computers creates new opportunities to apply advanced computational methods such as natural lan¬guage processing (NLP) and machine learning to the extraction of information from data embedded in free-text clinical notes (Szlosek et al., (2016), EGEMS (Wash DC). 4, 1222; Carrell et al., (2014), Am J Epidemiol. 179, 749-758; Deo., (2015), Circulation.132, 1920-1930; Yim et al., (2016), JAMA Oncol. 2, 797-804). Two main approaches to NLP information extraction exist. Rule-based extrac¬tion uses a predesigned set of rules that can take the form of characteristics or keywords. This approach works well for smaller defined sets of data such as when searching for all the brand names of a generic medication (e.g., if X is present, then Y=1) (Barrett et al., (2009), Stud Health Technol Inform. 143, 441-446; Lindvall C., (2017)). How¬ever, rule-based approaches fail when the desired in¬formation appears in a large variety of contexts within the free text (Yala et al., (2017), Breast Cancer Res Treat. 161, 203-211). This is extremely problematic for analysis of symptoms documented within EHRs, because clinicians use such variable terminology to describe how patients feel.

In contrast to rule-based NLP, machine learning NLP models do not depend on predefined set of rules. Rather, these algorithms learn patterns from a labeled set of free-text notes and apply these self-learned rules to future, non-labeled data sets (Kholghi et al., (2016), J Am Med Inform Assoc. 23, 289-296; Skeppstedt et al., (2014), J Biomed Inform. 49, 148-158; Roberts et al., (2013), J Am Med Inform Assoc. 20, 867-875). Labeled data means information associated with a definitive outcome. For example, if patients are routinely screened for depression at healthcare visits, a machine learning approach would begin to identify what characteristics within a record or text note are associated with having, or not having, the diagnosis of depression. A machine learning-based approach works well for tasks for which the set of extraction rules is very large, unknown, or both. Clinicians describe patient symptoms in highly variable ways, thus lending itself perfectly to machine learning.

Figure 1:
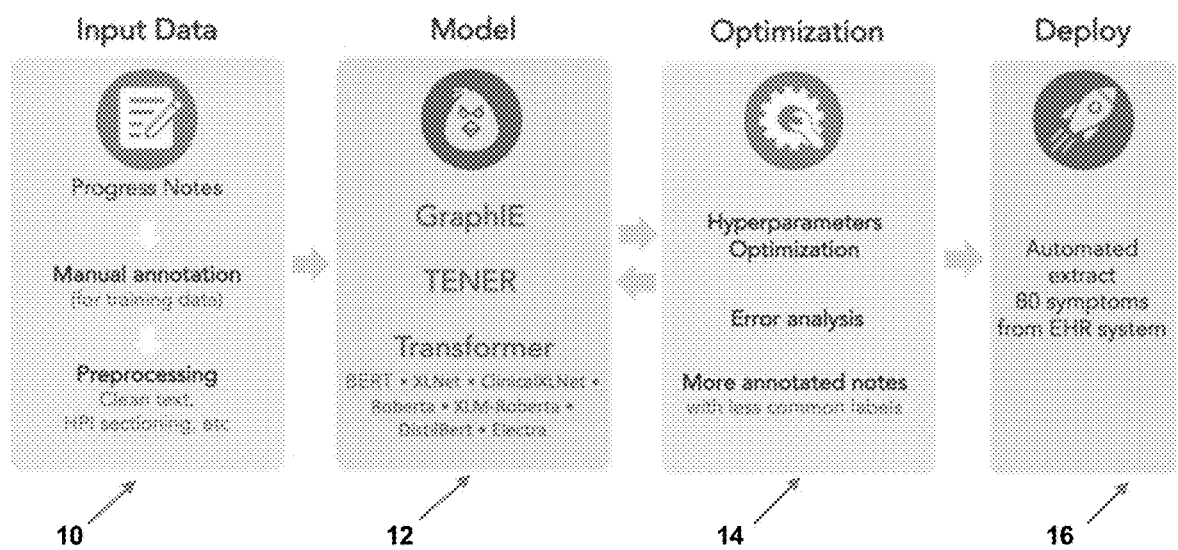
FIG. 1 illustrates conceptually a pipeline process derivation of a text data set and machine model, and training and testing the same, in accordance with the disclosure.
Figure 4:
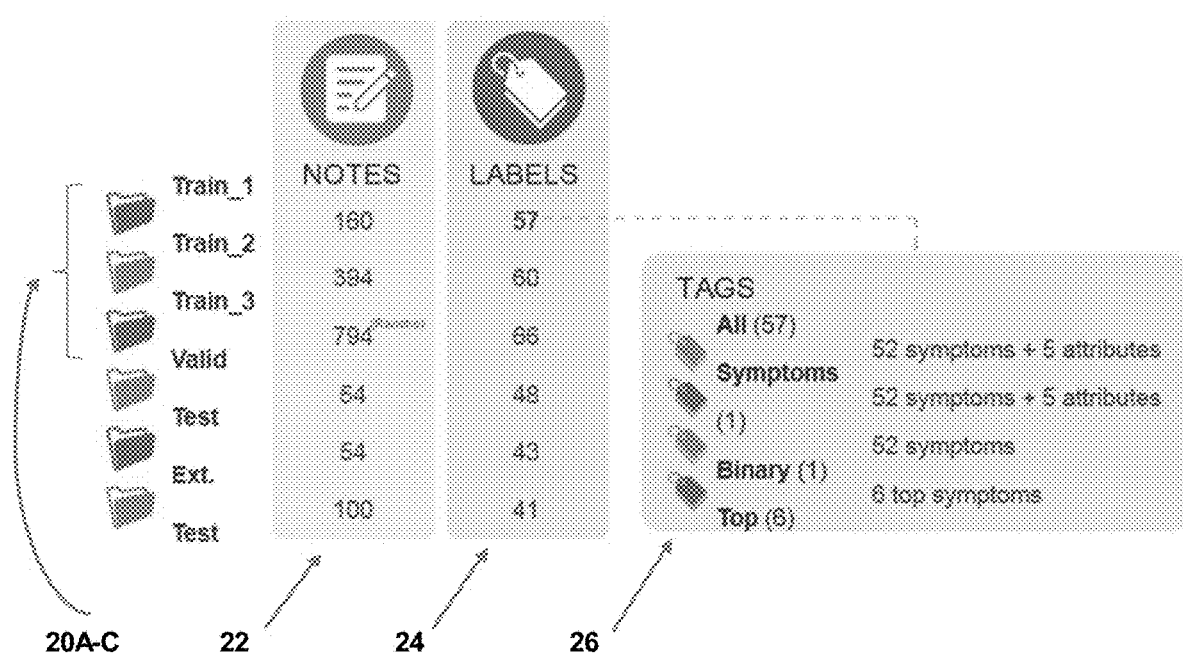
FIG. 4 illustrates conceptually an illustrative data set and the relationship between notes, labels and tags in accordance with the disclosure.

FIG. 1 illustrates conceptually a multiphase process for derivation of a text data set and a machine model, and training and testing the same, in accordance with the disclosure. In the first phase of the process, one or more sets of text data are derived from specially chosen progress notes which are then preprocessed by cleaning and segmenting the text and manually annotating, with labels and attributes, possible symptom terms, resulting in a text date set 10. The text data set 10 may comprise multiple training file subsets 20A-C, as illustrated in FIG. 4. In the next phase, a large portion of the preprocessed text data set is processed using one or more NLP modeling tools 12 to extract labeled symptom terms within the text data set 20A. The results of the extraction process are measure according to multiple parameters. In the next phase 16, another smaller portion 20B of the preprocessed text data set with less common labels is processed using the same NLP modeling tool 12 for hyperparameter optimization of the model. In the last phase 18, the optimized NLP modeling tool is used to extract labeled symptom terms from an as yet tested portion of the text data set 20C. The final extraction process performance is used to determine the frequency of various symptom terms and may be optionally compared with the gold-standard manual chart review.

Prior to extraction symptom terms with a deep NLP algorithm, the symptom of a pathology need to be defined and their respective definitions operationalized. This type of activity can be done by an expert panel of any of palliative care clinicians and researchers, computer programmers, artificial intelligence and machine learning experts, and medical trainees through discussion and consensus. To that extent, prior to coding, possible symptoms need to be categorized as positive (present), negative (absent), or context-dependent. "Present" indicates symptoms the clinician assessed and the patient endorsed (e.g. chest pain, fatigue, palpitations, or vomiting). For present symptoms, modifiers such as words or terms addressing a symptom's frequency or severity (e.g. controlled, decreased, extreme, frequent, reduced, or stable) are also typically annotated. "Absent" indicates symptoms that the clinician assessed but the patient did not endorse (e.g. denied chest pain, denied shortness of breath). Each absent symptom is typically annotated with a corresponding negation, the specific word/term indicating the absence of that symptom (e.g. denies, free, resolved, without).

Figure 2:
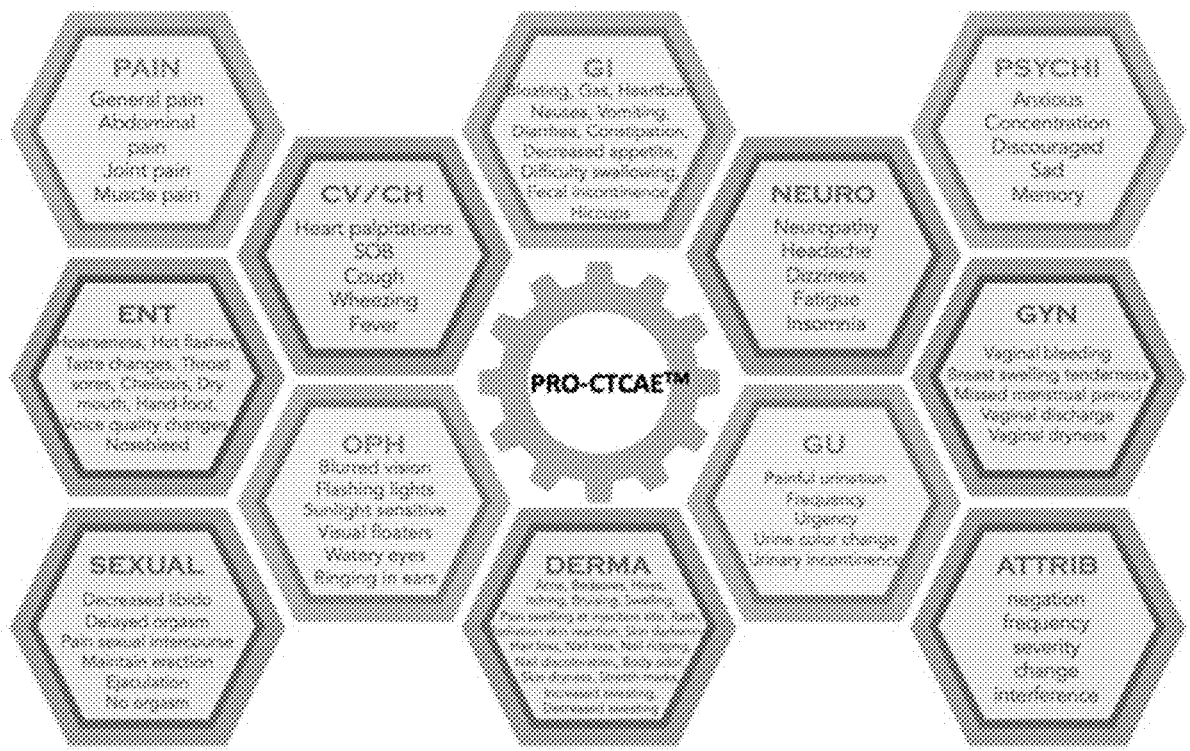
FIG. 2 illustrates conceptually an illustrative predefined set of symptoms and labeling attribute useful with the methods in accordance with the disclosure.

In addition to or alternatively to the foregoing symptom definition process, a predefined set of symptoms and labeling attributes 25 may be used with the methods in accordance with the disclosure. FIG. 2 illustrates conceptually the PRO-CTCAE Measurement System. The PRO-CTCAE is a patient-reported outcome (PRO) measurement system developed to evaluate approximately 80 symptomatic toxicity in patients on cancer clinical trials and was designed to be used as a companion to the Common Terminology Criteria for Adverse Events (CTCAE), the standard lexicon for adverse event reporting in cancer clinical trials. PRO-CTCAE items also evaluate the symptom attributes of frequency, severity, interference, amount, presence/absence, with each adverse event further assessed by up to three attributes. Examples of attributes are as follows:

Interference—symptom interferes with the patient's daily activities:
"The abdominal pain persistent but not interfering his work"
"The pain resulting in the inability to carry on any physical activity"
"He has severe cough and wakes him up several times at night."
Negation—no, denie(s|d), resolved, not likely, not any more;
Frequency—once a week, intermittent, occasionally, frequently, constantly, persistent, chronic, acute;
Severity—mild, moderate, severe, significant, profound, intolerable, adequate managed, very much, a little bit;
Change—improv(ed|ing), worse(ning), resolving, getting better, exacerbation, more, less.

Figure 3:
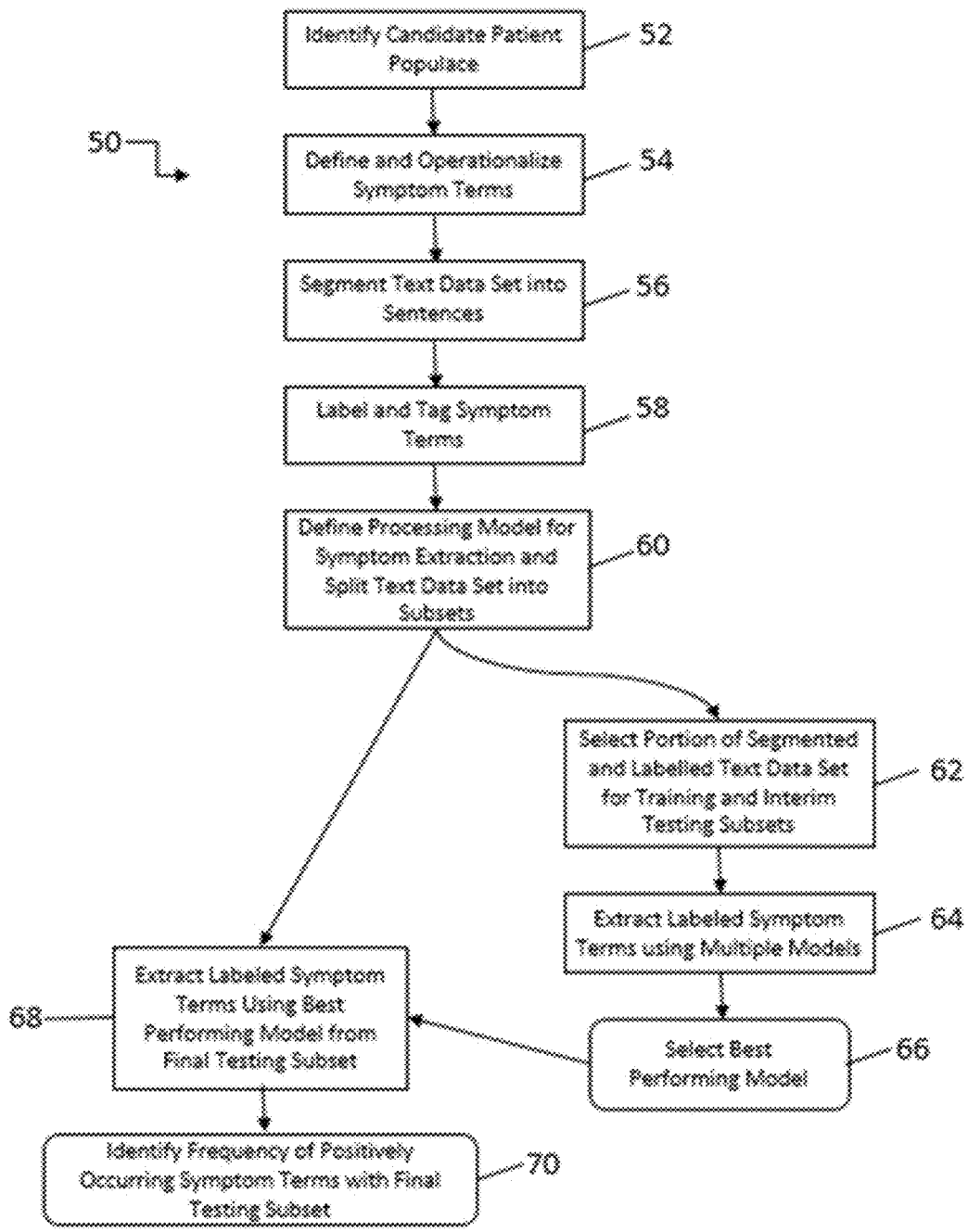
FIG. 3 illustrates conceptually a flowchart of a process for derivation of a text data set and machine model, and training and testing the same, in accordance with the disclosure.

FIG. 3 illustrates conceptually a flowchart 50 of the method for derivation of a text data set, and developing a codebook and machine model, and training and testing the same derivation on the text data set, in accordance with embodiments of the disclosure. To begin, according to a first exemplary method, clinical notes of patients receiving a therapeutic for a particular pathology were examined, as illustrated by process block 52. Such information can be can be stored in a centralized repository of clinical and administrative data. From this cohort, a random sample of patients may be selected and all their clinical notes obtained and stored electronically either in local computer system memory or in memory accessible over any number of different network infrastructures. Within this sample, patients meeting a common criteria, e.g. those who received at least one dose of a therapeutic, are identified and a data set created with all clinical notes of a common time period, e.g. from the first administration of the therapeutic until ninety days after the last documented dose. Next, symptom of a pathology are defined and their respective definitions operationalized in a manner as previously described and as illustrated by process block 54. The clinical notes may then be segmented into individual sentences using a software tool, such as the Punkt Sentence Tokenizer in Python's Natural Language Toolkit, resulting in a plurality sentences, as illustrated by process block 56, which comprise a text data set 10 for a machine learning model.

Next, with the ultimate goal of having a natural language processing identify symptom term occurrence within notes, each word in the text data set is manually labeled and tagged, using a software tool, as illustrated by process block 58. In the illustrative process, each word in the data set may be manually tagged with either a "positive," "neutral," or "negative" tag. These coding rules, e.g., a code book, may be developed by practitioners or experts or may have been previously defined, as describer with reference to process block 54 and FIG. 2. In embodiments, a word tagged with a "positive" status indicates the presence of a symptom term. A word tagged with a "neutral" status indicates a term unrelated to a symptom term. A word tagged with a "negative" status specifically indicates the absence of a symptom term. For example, using the foregoing code rules, in the sentence "patient describes having nausea, vomiting, and pain", the tags for that sequence of words would be ["neutral," "neutral," "neutral," "positive," "positive," "positive" ]. In the sentence "patient denies having nausea" the tags would be ["neutral," "neutral," "neutral," "negative" ].

Next, a practitioner labeled each word documented in 10,000 sentences obtained from the clinical notes of the randomly selected patients using the previously described coding specification, as also illustrated by block 58. Word phrases were labeled "positive" when they indicate that a symptom was reported either acutely or chronically. For example in the sentence "she has had abdominal pain and bloating for 7 months," symbols may be manually entered at the beginning and end of symptom term descriptions, that is, "she has had $1$abdominal pain and bloating$1/$ for 7 months." Word phrases may be identified as "negative" when the symptom is documented in the clinical notes, but is not experienced by the patient. For example, "she denies $-1$chest pain or shortness of breath$-1/$." Symptoms that are documented as well-controlled may be also labeled with a negative tag, for example, "pain is well-controlled." Symptoms term documented in a list, connecting words such as "and" and "or" may be also included with the corresponding tags. Misspelled words and abbreviations may be included in their original formats. For example, where "N/V" represents both nausea and vomiting as two symptoms, such symptom term may be represented as a single tag. Symptom terms mentioned in a medication list such as "take Tylenol for pain" may remain unlabeled, and, therefore, have a neutral status. Notes copied and pasted from previous entries may be labeled accordingly, regardless of repetition. All words that contribute toward describing a certain symptom term form part of the label, for example, "not eaten all day" or "unable to keep food down." Any words not tagged, with either of the positive or negative symptom tags, i.e., $1$, $-1$, respectively, are considered neutral in the machine learning algorithm. The result of the foregoing processes results in a labeled text data set which may be stored in system memory.

In embodiments, not every word or phrase within a free running segment of notes 22 in one of the text data sets 20A-C is given a label 24 and tag 26, but only those words or phrases that identify a symptom term, e.g. a symptom defined as part of the codebook, or a context which may be used to interpretation of the symptom term. FIG. 4 illustrates conceptually an exemplary data set and the relationship between notes, labels and tag in accordance with the disclosure. Note that the text data set have been divided into separate groups to facilitate initial training and fine tuning of the performance of a NLP extraction process.

In embodiments, annotation process described herein generates output files 30 that contain the labels and the positions of labels 32 within the clinical text data set, as illustrated in FIG. 5. These output files 30 are processed by one or more deep learning algorithms for training purposes to identify documentation of symptoms in the EHR.

Conditional Random Field Model

To build a model that can identify words within a sentence that represent symptom terms, a Conditional Random Field (CRF) model 12 may be developed, using the Python pycrf-suite software library, a Python wrapper for CRFsuite, as illustrated collectively by process blocks 60, 62 and 64. A CRF model as opposed to recurrent neural networks or bag-of-words techniques is chosen because recurrent neural networks need a larger training data set to work well and bag-of-words models would have made it difficult to generate results at the word level. CRFs were introduced in 2001 by Lafferty, McCallum, and Pereira as an alternative to hidden Markov models and maximum entropy Markov models, specifically for NLP sequence-labelling tasks such as part-of-speech tagging (Lafferty et al., (2001), Proc Eighteenth Int Conf Mach Learn. 1, 282-289). Markov models predict the sequence of a series of independent events based on their individual probabilities, whereas CRFs predict events based on multiple related events together and combinations of those events. In the task, the probability that a given word will indicate a symptom term depends not only on the word itself but on previous words. For example, in the partial sequence "patient denies having," the next word will likely have a negative status tag even before the next word is evaluated. Lafferty, McCallum, and Pereira define a CRF for observation variables X (e.g., words and their additional features) and random variables Y (e.g., part-of-speech word tags), as follows:

Let G=(V, E) be a graph such that Y=(Y $_v$) $_{v \in}$ v, so that Y is indexed by the vertices if G. Then (X, Y) is a CRF in case, when conditioned on X, the random variables Y$_v$ obey the Markov property with respect to the graph: $p$ (Y$_v$|X, Y$_\omega$, $\omega \neq v$)=$p$ (Y $_v$|X, Y$_\omega$, $\omega \sim v$), where $\omega \sim v$ means that $\omega$ and v are neighbors in G For each word in a sentence, as illustrated by process block 60, the following features may be used to capture English inflections: a bias term, lower-case word, the last three characters of the word, the last two characters of the word, whether the word is title-case, and whether the word is a number. For each word, the lower-case previous word, whether the previous word is upper-case, and whether the previous word is title-case or the "beginning of a sentence" tag instead if appropriate is included. Similarly, the same features regarding the next word in the sentence or an "end of sentence" tag, if the word was at the end of the sentence, may be included.

Simple random sampling is used to divide the labeled text data set 10 into training 20A, validation 20B, and test data sub-sets 20C, respectively. A fractional portion of the labeled text data set, e.g. 20%, may be held out for the test data set, which may be used to determine the final model performance, and thus excluded from model development or tuning processes. Of the remaining fractional portion, e.g. 80%, 80% of the remaining portion may be used as training data and 20% was used as validation data for selecting CRF hyperparameters and to select the final word features. Once the final model is selected, as illustrated by process blocks 62 and 64, a CRF model 12 may be trained using the entire 80% of test data sub-sets for training and validation and then tested using the test data sub-sets, as illustrated by process block 68.

The final CRF model performance was compared with the gold-standard manual chart review, as illustrated by process block 70. The performance metrics used for machine learning models include precision (positive predictive value), recall (sensitivity), and accuracy, where TP is the Total Positive, FP is the Found Positive, TN is the Total Negative, and FN is the Found Negative.

$$\text{precision} = \frac{TP}{TP+FP}$$

$$\text{recall} = \frac{TP}{TP+FN}$$

$$\text{accuracy} = \frac{TP+TN}{TP+TN+FP+FN}$$

The F1 score is another measure of a model's accuracy and is calculated as follows:

$$F_1 = 2 * \frac{1}{\frac{1}{\text{recall}} + \frac{1}{\text{precision}}} = 2 * \frac{\text{precision} * \text{recall}}{\text{precision} + \text{recall}}$$

Figure 6:
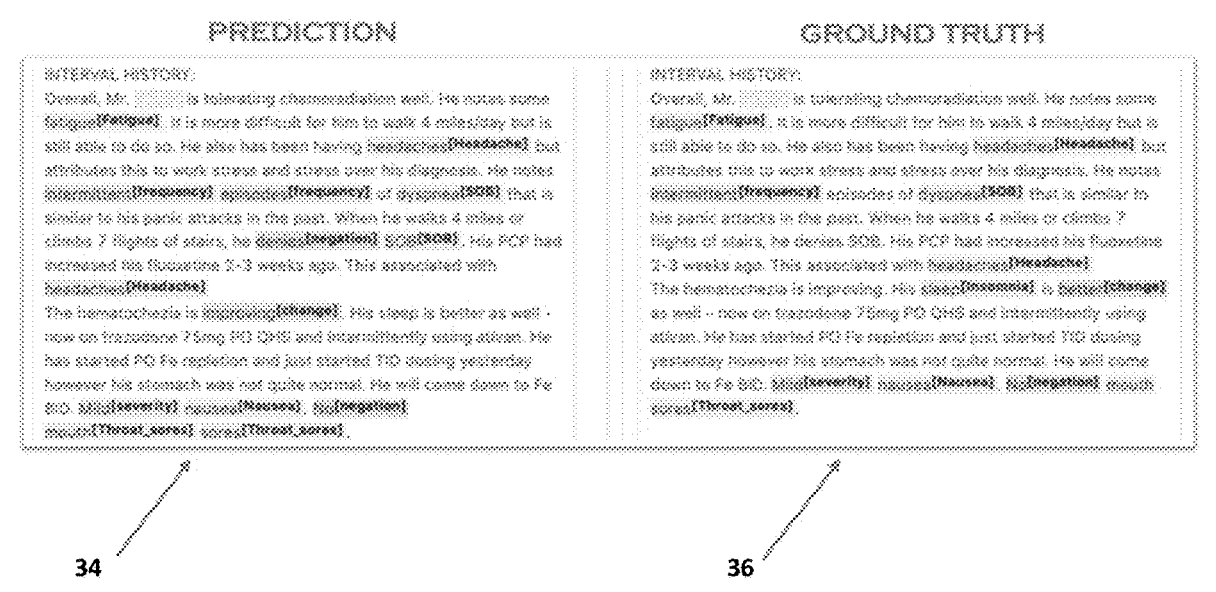

As such, the F1 score is the harmonic average of the precision and recall, where an F1 score reaches its best value at 1 (perfect precision and recall) and worst at 0. FIG. 6 illustrates a side by side comparison symptom term in text as extracted automatically using the methods described herein and manually.

In embodiments of the disclosed process, a deep NLP algorithm, GraphIE, may be adapted to the clinical setting according to the standard three-step model of training, validation, and testing. While many NLP algorithms analyze the precise sequence of words in a text by abstracting associations between words based on their relative distance from one another, GraphIE utilizes a graphical structure to abstract relations between words which may exist beyond their sequential positioning, enabling the analysis of both sentence-level patterns as well as more global, non-sequential patterns in the spontaneous language used to describe patient symptoms in clinical notes. The algorithm encodes each clinical note as a set of sentences, and the algorithm labels words as being associated or unassociated, with phrases indicating symptoms. Each note is thus represented by its own graphical structure, with each word being a node, or point, on the graph, and the words' associations with one another represented as edges, or connections, between the word nodes. Once the graph is built, the algorithm is trained to associate both local sequential and non-local coreferential dependencies between the words and the symptoms to which the words may refer. These graphs are then decoded back to their spontaneously written text-based format, with word labeling derived from the characteristics of the graphical representation. Code and further documentation are available at https://github.com/thomas0809/GraphIE.

In embodiments of the disclosed process, a deep NLP algorithm, BERT, may be adapted to the clinical setting according to the standard three-step model of training, validation, and testing. BERT stands for Bidirectional Encoder Representations from Transformers and is designed to pre-train deep bidirectional representations from unlabeled text by jointly conditioning on both left and right context. As a result, a pre-trained BERT model can be fine-tuned with just one additional output layer to create state-of-the-art models for a wide range of NLP tasks. For a given token, its input representation is constructed by summing the corresponding token, segment, and position embeddings for which BERT has specific set of rules to represent the input text for the model. In embodiments, in place of or in addition to the NLP tools disclosed herein, other NLP process agents or tools may likewise be used, including, but not limited to, XLNet, ClinicalXLNet, Roberta, XLM Roberta, DistilBert and Electra.

Computational Environment

The above described techniques may be implemented in a computing environment including a computer system in communication with one or more other computing devices and/or a data store via a network infrastructure. In an illustrative embodiment, the computing system may be implemented with one or more of a wide variety of computing devices including, but not limited to, personal computing devices, laptop computing devices, hand-held computing devices, terminal computing devices, mobile devices, wireless devices, various electronic devices and appliances and the like.

Any of the electronic health record data, or other data derived therefrom, may be stored in any storage device capable of maintaining data, including a single data storage device or a plurality of data storage devices. Such data storage device(s) may include, but are not limited to, static and dynamic memories, magnetic storage devices, solid state memory devices, and the like.

A communications network may be used to facilitate exchanging data between the various components in the computing environment. Exemplary network infrastructures may include, but are not limited to, wide area networks and local area networks using either cable media or wireless media.

Any of the process steps described herein may be implemented with computer executable instructions in the form of separately executable modules operating on the computer system. Such computer executable instructions may be implemented in the form of a computer program product. The implementation can, for example, be in a machine-readable storage device, for execution by, or to control the operation of, data processing apparatus. The implementation can, for example, be a programmable processor, a computer, and/or multiple computers.

In illustrative embodiment, a computer executable computer program may be provided in any form of programming language, including compiled and/or interpreted languages, and the computer program can be deployed in any form, including as a stand-alone program or as a subroutine, element, and/or other unit suitable for use in a computing environment.

Method steps, as disclosed herein, can be performed by one or more programmable processors executing a computer program to perform functions of the invention by operating on input data and generating output. Method steps can also be performed by and an apparatus can be implemented as special purpose logic circuitry. The circuitry can, for example, be a FPGA (field programmable gate array) and/or an ASIC (application-specific integrated circuit). Subroutines and software agents can refer to portions of the computer program, the processor, the special circuitry, software, and/or hardware that implement that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data.

Information carriers media suitable for embodying computer executable instructions and data include all forms of non-volatile memory, including by way of example EPROM, EEPROM, flash memory devices, magnetic disks, internal hard disks, removable disks, magneto-optical disks, CD-ROM, and/or DVD-ROM disks.

The above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of data communication network, including local area network (LAN), a wide area network (WAN), the Internet, wired networks, and/or wireless networks.

FIG. 1 illustrates a prior art system architecture for a computer system 100 on which the methods described herein may be implemented. The exemplary computer system of FIG. 1 is for descriptive purposes only. Although the description may refer to terms commonly used in describing particular computer systems, the description and concepts equally apply to other systems, including systems having architectures dissimilar to FIG. 1.

Computer system 100 includes a central processing unit (CPU) 105, which may be implemented with a conventional microprocessor, a random access memory (RAM) 110 for temporary storage of information, and a read only memory (ROM) 115 for permanent storage of information. A memory controller 120 is provided for controlling RAM 110. A bus 130 interconnects the components of computer system 100. A bus controller 125 is provided for controlling bus 130. An interrupt controller 135 is used for receiving and processing various interrupt signals from the system components.

Mass storage may be provided by a removable media drive 142. Data and software may be exchanged with computer system 100 via removable media such as diskette 142 and CD ROM 147. Diskette 142 is insertable into diskette drive 141 which is, in turn, connected to bus 30 by a controller 140. Similarly, CD ROM 147 is insertable into CD ROM drive 146 which is, in turn, connected to bus 130 by controller 145. Hard disk 152 is part of a fixed disk drive 151 which is connected to bus 130 by controller 150.

User input to computer system 100 may be provided by a number of devices. For example, a keyboard 156 and mouse 157 are connected to bus 130 by controller 155. An audio transducer 196, which may act as both a microphone and a speaker, is connected to bus 130 by audio controller 197, as illustrated. It will be obvious to those reasonably skilled in the art that other input devices, such as a pen and/or tabloid may be connected to bus 130 and an appropriate controller and software, as required.

DMA controller 160 is provided for performing direct memory access to RAM 110. A visual display is generated by video controller 165 which controls video display 170. Computer system 100 also includes a communications adapter 190 which allows the system to be interconnected to a local area network (LAN) or a wide area network (WAN), schematically illustrated by bus 191 and network 195.

Operation of computer system 100 is generally controlled and coordinated by any number of commercially available operating system software that controls allocation of system resources and performs tasks such as processing scheduling, memory management, networking, and I/O services, among things. In particular, an operating system resident in system memory and running on CPU 105 coordinates the operation of the other elements of computer system 100. One or more applications such as those described herein may execute under the control of the operating system.

The computer system of FIG. 1, may be implemented as part of a hybrid telecommunication environment including packet-switched data networks, such as the Internet and private Intranets, as well as apparatus bridging between the two, and to which other computer systems may be coupled, directly or indirectly, to the network 195. These computer systems may be implemented with a computer architecture similar or dissimilar to that described with reference to FIG. 1.

Any of the text data set 10, subsets 20A-C, NLP process module 12, notes 22, labels 24, tags 26, output files 30 and processing code 32, and results 34, 36 and 40, including symptom frequency counts and correlations with specific symptom terms, may be stored in any of system RAM 110, disk drive 152 of computer 100 or any memory accessible via network 195. NLP process module 12 may be executable on CPU 105 of computer 100.

Example 1

FIG. 5 illustrates conceptually a flowchart 100 of the method for derivation of a text data set, and developing a codebook and machine model, and validation of the same, in accordance with Example 1, where RPDR=Research Patient Data Registry. To begin, clinical notes of patients receiving paclitaxel-containing chemotherapy for breast cancer were examined. This population was chosen as a test case because paclitaxel is one of the most commonly administered chemotherapy regimens for solid tumors, and because patients often experience symptoms during chemotherapy. Candidate records were obtained from the Research Patient Data Registry (RPDR) and a centralized repository of clinical and administrative data from hospitalized patient and outpatient encounters at Partners HealthCare (Weiss et al., (2016), J Pers Med. 6, 13). Approximately 84,230 breast cancer (International Classification of Diseases, Ninth Revision, Clinical Modification codes 174.9 and 175.9) patients available in RPDR between May 1996 and May 2015 were identified. From this cohort, a random sample of 4732 patients were selected and all their clinical notes were obtained and stored in system memory. Within this sample, 2695 patients who received at least one dose of a paclitaxel-containing chemotherapy were identified. A data set with all clinical notes from the first administration of paclitaxel until 90 days after the last documented dose was then created. The clinical notes were then broken into individual sentences using the Punkt Sentence Tokenizer in Python's Natural Language Toolkit, resulting in 103,564 sentences which comprised the data set for the machine learning model.

With the ultimate goal of having a natural language processing identify symptom occurrence within notes, each word in the data set was tagged with either a "positive," "neutral," or "negative" tag in the manner as described previously herein. A physician labeled each word documented in 10,000 sentences obtained from the clinical notes of 39 randomly selected patients receiving paclitaxel using the coding specification. Phrases were labeled "positive" when they indicate that a symptom was reported either acutely or chronically. Examples of this include "she has had abdominal pain and bloating for 7 months." Symbols were manually entered at the beginning and end of symptom descriptions, that is, "she has had $1$abdominal pain and bloating$1/$ for 7 months." Phrases were identified as "negative" when the symptom was documented in the clinical notes, but was not experienced by the patient. For example, "she denies $-1$chest pain or shortness of breath$-1/$." Symptoms that were documented as well-controlled were also labeled with a negative tag, for example, "pain is well-controlled." When symptoms were documented in a list, connecting words such as "and" and "or" were also included with the corresponding tags. Misspelled words and abbreviations were included in their original formats. Where "N/V" represents both nausea and vomiting as two symptoms, this is represented as a single tag. Symptoms mentioned in the medication list such as "take Tylenol for pain" were not labeled, so these words remained neutral. Notes that were copied and pasted from previous entries were labeled accordingly, regardless of repetition. All words that contributed toward describing a certain symptom formed part of the label, for example, "not eaten all day" or "unable to keep food down." The words which were not tagged, with either of the positive or negative symptom tags (i.e., $1$, $-1$, respectively), were considered neutral in the machine learning algorithm.

A Conditional Random Field Model (CRF) was developed using the Python pycrf-suite software library, a Python wrapper for CRFsuite. Simple random sampling was used to divide the labeled data set into a training, validation, and test data set. Approximately 20% of the labeled data set was held out for the test data set, which was used to determine the final model performance, and thus excluded from model development or tuning. Of the remaining 80%, 80% was used as training data and 20% was used as validation data for selecting CRF hyperparameters and to select the final word features. Once the final model had been selected, a CRF model was trained using the entire 80% of the labeled data set used for training and validation and tested using the performance on the held-out 20% sample.

Table 1-1 below shows the patient characteristics of the total sample and the subsample used for CRF model building and testing. Most patients were non-Hispanic white women. The mean age at the time of chemotherapy was 50 years for the total sample and 56 years among the labeled sample. The most commonly used chemotherapy in combination with paclitaxel were doxorubicin and cyclophosphamide.

Table 1-2 shows the performance of the final model on the 20% held-out test data set. The CRF model identified 69% negative symptoms and 56% positive symptoms originally identified by gold-standard chart review. Overall, precision, recall, and F1 scores were higher for negative symptoms compared with positive symptoms. The positive predictive value was high for both negative and positive symptoms, the non-neutral labels, at 89% and 82%, respectively, indicating that most symptoms identified by the CRF model were correctly labeled. The model identified all neutral labels (sensitivity 100%), that is, words not describing symptoms. Neutral words were never misclassified as describing a symptom.

The overall accuracy of the final CRF model was 99.2%. The vast majority of labels were neutral. The high precision, recall, and F1 score associated with the neutral label thus led to very high accuracy for the model overall. Precision, recall, and F1 score were lower for positive and negative labels, which were the primary focus of this study.

A qualitative comparison of human versus machine-based labeling of symptoms showed that the machine often mislabeled vague descriptions of symptoms as neutral (e.g., urination is sometimes slow), which reduced the sensitivity of the final CRF model. The CRF model also misclassified stable symptoms as positive while the human coder labeled these as negative (e.g., pain is currently controlled). The model performed well at correctly labeling common descriptions of symptoms (e.g., pain, nausea, n/v, vomiting, sob, dyspnea). The model also performed well at correctly labeling symptoms following the words "no" or "denies" as negative. Examples of sentences labeled by a human versus machine are shown in FIG. 6.

TABLE 1-1

| Patient Characteristics | Total Sample (n = 2695) | Labeled Sample (n = 39) |
| --- | --- | --- |
| Age, yrs, mean (SD) | 50.33 (11.18) | 55.60 (10.89) |
| Female, % | 98.9 | 97.4 |
| Non-Hispanic white, % | 78.05 | 74.36 |
| Chemotherapy,[a] % | | |
| Paclitaxel | 100.0 | 100.0 |
| Doxorubicin | 82.9 | 51.3 |
| Cyclophosphamide | 82.1 | 38.5 |

[a]Three most frequently used chemotherapies.

Figure 8:
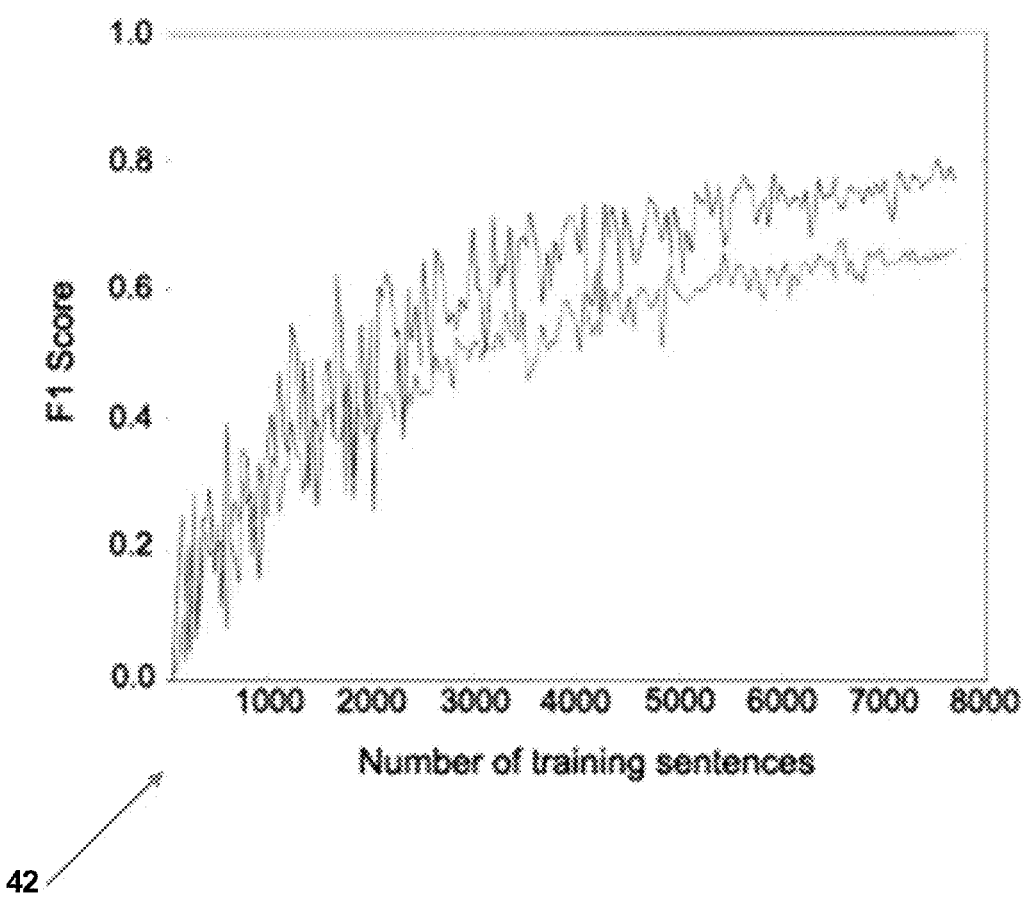
FIG. 8 illustrates a learning curve analysis of the degree to which the CRF model's F1 score improved in response to additional training data in accordance with Example 1 of the disclosure.
Figure 9:
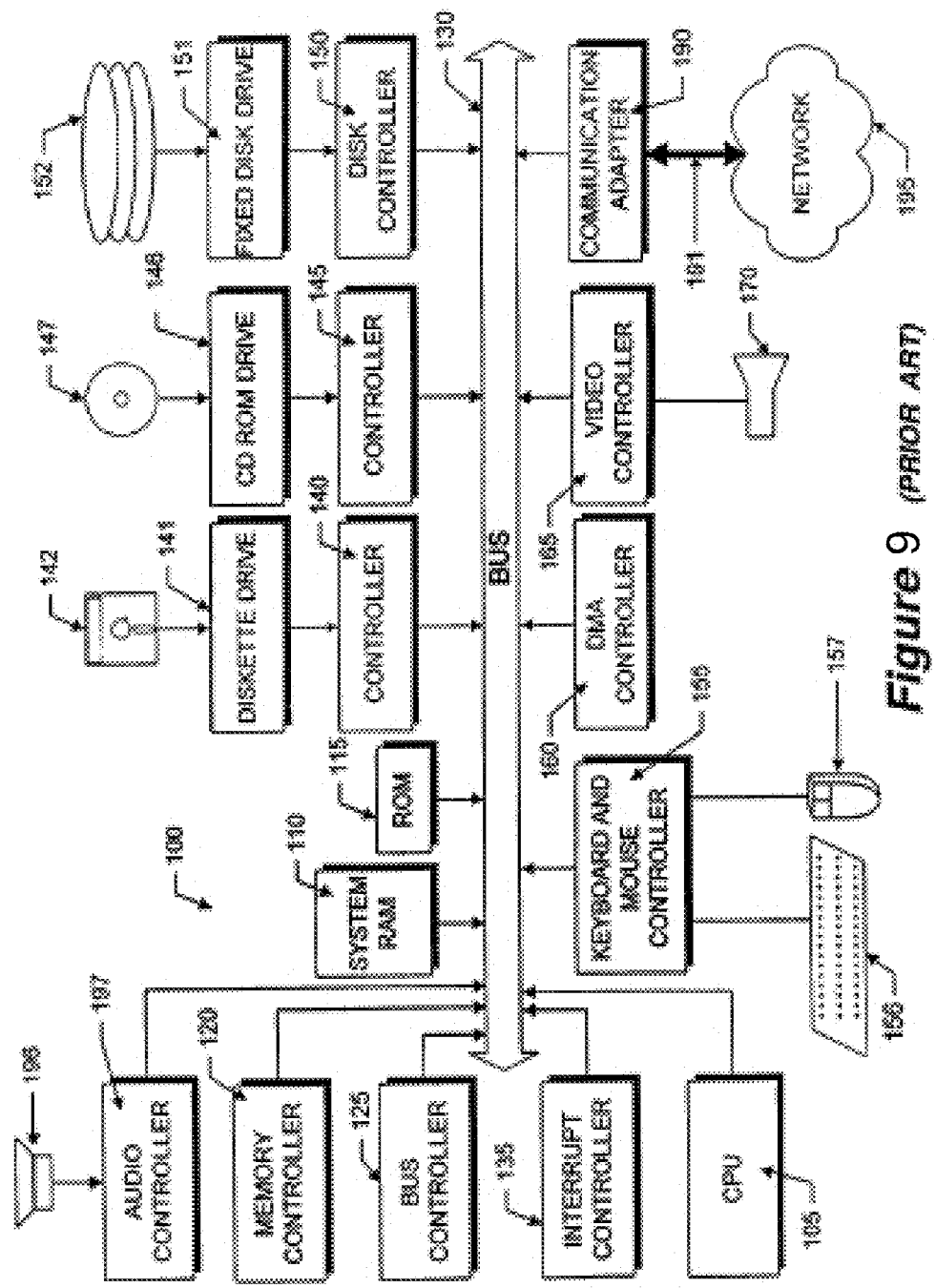
FIG. 9 illustrates conceptually block diagram of a prior art computer system and network infrastructure that may be utilized with the methods in accordance with the disclosure.

FIG. 8 is a graph 42 illustrating how the learning curve analysis of the degree to which the CRF model's F1 score improved in response to having more training data. As expected, the positive and negative label F1 scores increased significantly from the first few hundreds of training sentences, and then increased more slowly as additional data were added. The neutral label F1 score remained near 1.0, but exhibited a visible increase over the first few hundred sentences as well. Lastly, the F1 score for negative labels became distinctly higher than those for positive labels after the first 5000 training sentences.

TABLE 1-2

CRF Model Performance on Held-Out Test Sample of Labeled Sentences With 95% Cls for Precision and Recall

| | Precision[a] | | Recall[b] | | F1[c] |
| --- | --- | --- | --- | --- | --- |
| Positive | 0.82 | (0.78 0.86) | 0.56 | (0.52 0.60) | 0.66 |
| Negative | 0.86 | (0.82 0.90) | 0.69 | (0.64 0.74) | 0.77 |
| Neutral | 0.99 | (0.99 0.99) | 1.00 | (1.00 1.00) | 1.00 |

[a]Same as positive predictive value.
[b]Same as sensitivity.
[c]Harmonic mean of precision and recall.

After assessing the CRF model performance, the model was applied to the total sample of 103,564 sentences obtained from the beginning to 90 days after paclitaxel treatment. The model identified 86 different descriptions of symptoms. Table 1-3 shows the frequency of the 20 most commonly machine-extracted symptoms and their frequencies. Several of the 20 symptoms are known side effects from paclitaxel treatment. The most common positive symptom was pain followed by fatigue and nausea. The most common positive and negative symptom was pain. In total, the CRF model identified 19,145 words describing symptoms: 9840 positive and 9305 negative symptoms. The machine-based labeling of 103,564 sentences took two minutes when run on an interactive node on the ERIS. One cluster system, which was roughly equivalent to running code on a laptop (i.e., consumer-grade CPU, running single-threaded code, with reasonable memory constraints of 4-8 GB). In contrast, manual labeling of 10,000 sentences took 42 person hours.

Computational methods such as NLP and machine learning enable the extraction of information from data embedded in free-text clinical notes. In this study, a CRF model was built and tested to identify words describing active symptom (positive label), absence of a symptom (negative label), or not a symptom (neutral label) in the clinical notes of breast cancer patients receiving chemotherapy. The algorithm learned to identify symptoms by training on a data set manually annotated by a physician. Compared with the gold-standard manual coding, the final computer model identified 56% of positive and 69% of negative symptom labels with a precision of 82% and 86%, respectively. The sensitivity was low because the CRF model did not perform well at identifying vaguely described or infrequently documented symptoms. However, the high model precision means that the vast majority of symptoms identified by the CRF model matched symptoms identified by the human coder. Importantly, the final computer algorithm was >12,000 faster at identifying symptoms in clinical notes than the human coder. The experience of using machine learning to extract symptoms from EHR documentation demonstrates both the feasibility and importance of this approach.

FIG. 6 is a side by side comparison of symptom terms in text 34 as extracted automatically and symptom terms in text 36 as extracted manually, illustrating examples of sentences with words labeled as symptoms terms by the human coder and the CRF model. Sentences were selected to include words mislabeled by the CRF model. Effective symptom management is associated with improved clinical outcomes, including reduced hospitalizations, quality of life, and survival benefits.

In FIG. 7 symptom terms in a text data segment 40 are indicated positive (red and italicized), negative (blue and bolded), and neutral (green) labels. Easy access to symptom data offers huge possibilities to improve quality care in serious illness. For example, using the disclosed methods one could correlate depression with medication use, associate radiological imaging patterns and nausea, or explore the connection between weight loss and fatigue. One use of the disclosed technique is to use a CRF model to track clinician screening for common cancer symptoms such as pain, nausea, and depression and integrate the methods with quality improvement projects.

In recent years, much effort has focused on developing Web or tablet-based systems for collecting symptom data directly from patients (Basch et al., (2017), JAMA. 318, 197-198). These systems hold great promise, yet are not routinely available and will always be limited by respondent burden and other exigencies. For instance, many hospitalized patients with cancer and other serious conditions will experience delirium or temporary illness that impairs their reporting ability and many seriously ill persons suffer from cognitive impairment (Grandahl et al., (2016), Nord J Psychiatry. 70, 413-417). Thus, improving detection of symptoms in medical records can augment the understanding of patient experience, especially where the validity of proxy symptom reporting has been questioned (Singer et al., (2015), Ann Intern Med.162, 175-183; Singer et al., (2016), J Palliat Med.19, 1066-1073). In previous research, pain elicited from patients was compared with that documented in EHRs. Patient-elicited reports were more sensitive, but clinicians tended to document more severe and therefore potentially more actionable pain (Lorenz et al., (2009), J Am Board Fam Med. 22, 291-298). Future research will need to compare implications of these modalities to understand when they have independent or conjoint clinical value.

The CRF model the performance can be improved with modifications to the methods. A qualitative review of the results indicated that a significant number of the model misclassifications stemmed from inconsistent labeling by the human coder. The performance of supervised machine learning algorithms is closely linked to the quality and generalizability of the labeled data set. In this study, the human coder labeled any word(s) that could represent a symptom, including ambiguous narrative descriptions (e.g., "not eaten all day"). Better performance might be achieved by setting stricter labeling guidelines depending on the target application of the model. For example, labeling only declarative statements regarding clearly present-time symptoms (e.g., nausea, vomiting) to generate a highly accurate model might miss narratively stated but important symptoms (e.g., not eaten all day). By modifying the methods used depending on the task, the approach could be tailored for several applications. For example, CRF models could be used to identify a cohort of patients experiencing specific symptoms, such as nausea and vomiting. The model's output (i.e., predictions of positive and negative symptoms) could also be used as components for additional machine learning models. For example, the probability of outcomes such as hospitalization or death could be predicted given a patient's current symptoms (Gupta et al., (2014), BMJ Open. 4, e004007; Kessler et al., (2015) JAMA Psychiatry. 72, 49-57).

TABLE 1-3

Frequency of the 20 Most Commonly Machine-Extracted Symptoms From the Total Sample of 103,564 Sentences

| Positive | Negative |
| --- | --- |
| Pain (2236) | Pain (1307) |
| Fatigue (662) | Chest (422) |
| Abdominal (539) | Chills (403) |
| Nausea (399) | Sob (375) |
| Back (296) | Vomiting (330) |
| Sob (294) | Cough (322) |
| Cough (277) | Nausea (318) |
| Discomfort (251) | Fevers (299) |
| Fever (220) | Diarrhea (284) |
| Vomiting (218) | Fever (251) |
| Chest (206) | Dysuria (211) |
| Breath (191) | Constipation (204) |
| Shortness (185) | Abdominal (193) |
| Appetite (157) | Palpitations (190) |
| Dyspnea (153) | Headache (184) |
| Edema (138) | Weakness (181) |
| Diarrhea (138) | Numbness (168) |
| v (134) | Appetite (160) |
| n (125) | Bleeding (156) |
| Weakness (115) | Weight (153) |

Several limitations must be highlighted. In the machine algorithm, it was sought to clearly define what does and does not constitute a symptom. However, in the free text, there were many ambiguous descriptions in which, for example, the text indicated a symptom, but in a narrative manner, the text indicated a historical symptom, or the text discussed a symptom, but did not clearly indicate whether the symptom was active. As mentioned above, machine performance would likely improve if the CRF model is trained on a data set labeled with more stringent symptom definitions. It would also help to investigate the accuracy of human labeling by having multiple physicians label the same notes and then calculating the frequency with which their labels agree.

Although the learning curve analysis in FIG. 3 shows diminishing returns with respect to the F1 score by the addition of training data, additional labeled data might increase model performance. In this study, only 10,000 sentences were labeled because manual labeling was time consuming and required physician time. A much larger training data set could allow the model to learn more of the infrequent ways symptoms may be expressed and, in particular, some of the more narrative symptom indications. It is important to develop infrastructure that allow for collaboration and data sharing between healthcare systems. A major opportunity with machine learning methods is that they can handle very large data sets and the models improve over time.

In summary, cancer patients accrue tens to hundreds of clinical notes during the course of their treatment, and manual review of every chart is costly, error prone, and infeasible. As a result, data documented in the clinical notes including patient experience and symptoms are rarely analyzed in a way that can be helpful to patient care and research. The Natural Language Processing and machine learning methods, such as the CRF model disclosed here, can be developed for use in applications for which data are not currently accessible.

Example 2

A random sample of clinical notes from a cohort of patients with Congestive Heart Failure (CHF) who later received Cardiac Resynchronization Therapy (CRT) was identified. Investigators labeled documented symptoms as present, absent, and context-dependent (pathologic depending on the clinical situation) to form a text data set. An algorithm was trained on 80% of the text data set and hyperparameters fine-tuned on another 10% of the text data set. The optimized model was tested on the remaining 10% of the text data set. The model's performance was compared to investigators' annotations using accuracy, precision (positive predictive value), recall (sensitivity), and F1 score (a combined measure of precision and recall). Investigators annotated 154 notes (352,157 words) and identified 1340 present, 1300 absent, and 221 context-dependent symptoms. In the test set of 15 notes (35,467 words), the model's accuracy was 99.4% and recall was 66.8%. Precision was 77.6% and overall F1 score was 71.8. F1 scores for present (70.8) and absent (74.7) symptoms were higher than that for context-dependent symptoms (48.3).

Study Population

Primary data source was the Partners HealthCare Research Patient Data Registry (29,30). The Research Patient Data Registry included data from 4.6 million patients collected over more than 20 years from multiple EHR systems at Partners HealthCare, a large healthcare system in Eastern Massachusetts. The database contains more than 227 million encounters, 193 million billing diagnoses, 105 million medications, 200 million procedures, 852 million lab values, and over 5 million unstructured clinical notes, including outpatient visit notes, inpatient admission and consultation notes, cardiology reports (e.g. EKGs and echocardiograms), and others.

Patients who underwent CRT implantation between January 2004 and December 2015 at Brigham and Women's Hospital and Massachusetts General Hospital were eligible. Cases were identified cases using International Classification of Diseases, Ninth Revision (ICD-9) and Current Procedural Terminology (CPT) codes for CRT: ICD-9 00.50, ICD-9 00.51, CPT 33224, CPT 33225, or CPT 33226. Patients who underwent initial implantation of either a CRT pacemaker (CRT-P) or CRT with implantable cardioverter defibrillator (CRT-D) were included. As this dataset was also used for a parallel study examining LVEF response to CRT placement, patients who lacked baseline measurement of LVEF within 60 days of the procedure or follow-up LVEF measurement between 6 and 18 months post-procedure and were alive at 18 months, or who received a CRT within 18 months of the end of the dataset's time window were excluded.

From this population, a random sample of discharge summaries from hospitalizations that were either prior to CRT-implantation, or from the admission during which the patient underwent the procedure was selected to create the text data set. Each discharge summary contained an admission History of Present Illness (HPI) and Review of Systems (ROS) that reflects the patient's symptom burden prior to undergoing CRT implantation during that hospitalization.

Symptom Coding and Categorization

Symptom annotation within the text data set was performed using a customized version of PyCCI, a local executable software program built using Python Version 3.5. Customized features included color highlighting and inclusion of associated modifiers to annotate symptoms, similar to that illustrated in FIG. 5. PyCCI's use during the annotation process allowed for the collection of annotation information necessary for the utilization of modern NLP algorithms, including information for benchmarking annotation speed comparisons between humans and machines.

Prior to coding, an expert panel of palliative care clinicians and researchers, computer programmers, artificial intelligence and machine learning experts, and medical trainees was convened. Through discussion and consensus, the panel categorized symptoms as positive (present), negative (absent), or context-dependent and operationalized their definitions. Present indicated symptoms the clinician assessed and the patient endorsed (e.g. chest pain, fatigue, palpitations, or vomiting). For present symptoms, annotators also coded modifiers, words or terms addressing a symptom's frequency or severity (e.g. controlled, decreased, extreme, frequent, reduced, or stable). Absent indicated symptoms that the clinician assessed but the patient did not endorse (e.g. denied chest pain, denied shortness of breath). Each absent symptom was also annotated with a corresponding negation, the specific word/term indicating the absence of that symptom (e.g. denies, free, resolved, without).

Context-dependent indicated any symptom describing "homeostatic" physiological functions such as appetite, sleep, or urination (e.g. decreased sleep, increased urination) that may or may not be pathologic depending on the patient's baseline condition. For example, weight gain could indicate either fluid accumulation due to worsening heart failure or an improvement in appetite due to decreased gut edema associated with a higher dose of diuretics. Context-dependent also included New York Heart Association (NYHA) heart failure symptom status (e.g. NYHA class II-III, CHF class II).

Once symptoms were defined, three members of the study team (annotators) reviewed each note in the dataset. Only the HPI and ROS sections of the note were coded. Other sections of the notes were not removed through preprocessing, but saved to evaluate the model's performance on notes with minimal human intervention.

After the annotators each coded 50 notes, a fourth investigator reviewed the annotations and resolved discrepancies. The PyCCI software allowed the reviewer to see words with coding concordance (highlighted in green) or discordance (highlighted in red). If the reviewer was unsure of how to resolve discordant coding, the study PI also provided input. The reviewer gave annotators feedback on areas of common disagreement, which they resolved through discussion and, when necessary, formalized into iterative coding "rules." Annotators repeated this process for each set of 50 notes. To account for the significant variability in how clinicians describe symptoms in free-text notes, the annotators and reviewer classified each annotated symptom based on common terminology (e.g. chest pain, abdominal pain, headache), used for the ROS in Epic® (Epic Systems, Inc).

A deep NLP algorithm, GraphIE, was adapted to the clinical setting according to the standard three-step model of training, validation, and testing. While many NLP algorithms analyze the precise sequence of words in a text by abstracting associations between words based on their relative distance from one another, GraphIE utilizes a graphical structure to abstract relations between words which may exist beyond their sequential positioning. This enable the analysis of both sentence-level patterns as well as more global, non-sequential patterns in the spontaneous language used to describe patient symptoms in clinical notes.

Briefly, the algorithm encodes each clinical note as a set of sentences, and the algorithm labels words as being associated or unassociated, with phrases indicating symptoms. Each note is thus represented by its own graphical structure, with each word being a node, or point, on the graph, and the words' associations with one another represented as edges, or connections, between the word nodes.

Once the graph is built, the algorithm is trained to associate both local sequential and non-local coreferential dependencies between the words and the symptoms to which the words may refer. These graphs are then decoded back to their spontaneously written text-based format, with word labeling derived from the characteristics of the graphical representation. Code and further documentation are available at https://github.com/thomas0809/GraphIE Data Analysis Clinical notes were quantitatively described by providing: 1) information about their length and vocabulary variance; 2) the average number per note of each symptom type; 3) the average character and word length of each symptom type, and the number of the related modifiers. The symptom distribution for each category was also calculated.

Following a common procedure in the NLP literature, the dataset was split into 80% clinical notes for training (Train), 10% for development (Dev) and 10% for testing (Test). The model's performance was calculated based on the test set and values for report accuracy, precision, recall, and the F1 score (the harmonic mean of precision and recall) and scores ranged from 0 (worst) to 1 (perfect precision and recall). These metrics were calculated according to standard formulas described in Forsyth A W, Barzilay R, Hughes K S, et al. Machine Learning Methods to Extract Documentation of Breast Cancer Symptoms From Electronic Health Records. J Pain Symptom Manage 2018; 55:1492-9. All data analysis was performed using Python version 3.5.

Results

The total dataset included 10,870 notes for 990 unique patients, from which were randomly extracted and annotated 154 discharge summaries for 115 patients, described in Table 2-1. The admission date for all hospitalizations summarized in the selected notes predates CRT-implantation.

TABLE 2-1

Baseline characteristics of study participants at the time of CRT-implantation
Characteristics, N = 115

| | |
|---|---|
| Age, mean years (SD) | 71.2 (12.2) |
| Male gender, n (%) | 93 (80.9) |
| Race | |
| White | 99 (86.1) |
| Non-White | 16 (13.9) |
| NYHA class[a], n = 49 (%) | |
| I | 1 (2.0) |
| II | 12 (24.5) |
| III | 36 (73.5) |
| IV | 0 |
| LVEF, mean % (SD) | 25.1 (7.5) |
| Heart rate, mean BPM (SD) | 84.1 (40.0) |
| QRS duration, mean ms (SD) | 158.1 (35.4) |
| Left bundle branch block, n (%) | 39 (33.9) |
| AV block, n (%) | 20 (17.4) |
| Afib, n (%) | 65 (56.5) |
| Renal disease, n (%) | 15 (13.0) |
| Baseline creatinine, mean mg/dL (SD) | 2.3 (2.8) |
| Diabetes, n (%) | 42 (36.5) |
| CRT response[b], n (%) | |
| Died within year | 34 (29.6) |
| Non-Responder | 17 (14.8) |
| Responder | 64 (55.6) |

NYHA = New York Heart Association LVEF = left ventricular ejection fraction
[a]66 patients missing NYHA functional classification information.
[b]CRT response: Non-responder = <0% improvement in LVEF 6-18 months following CRT, Response = ≥0% improvement in LVEF 6-18 months following CRT The characteristics of analyzed notes and most common annotated symptoms are described in Table 2-2. Notes were written by clinicians on the patient treatment team (e.g., physicians, nurse practitioners). Investigators annotated the HPI and ROS sections of discharge summaries, both of which the EHR automatically inserted into the discharge summary from the admission's initial History and Physical (H&P) note. Mean note length was 2,286 words, of which 882 words were unique. Mean number of symptoms per note was: 8.7 (SD 8.4) present, 8.4 absent (SD 11.5), and 1.4 context-dependent (SD 1.9). Documented length was similar for present and absent symptoms (mean 1.61 words, or 10.8 characters), while it was larger for context-dependent symptoms (mean 3.0 words, or 17.5 characters). Most commonly documented positive symptoms were "chest pain," "pain," "shortness of breath," "dyspnea," and "fatigue." Most commonly documented negative symptoms were "chest pain," "palpitations," "chills," "shortness of breath," and "abdominal pain." Most commonly documented context-dependent symptoms were "weight gain," "weight loss," "decreased appetite," "poor PO intake," "NYHA Class II symptoms," and "NYHA Class III symptoms." The distribution of annotated symptoms is depicted in Table 2-2.

TABLE 2-2

Characteristics of notes and investigator-annotated symptoms.

| | # reports | Avg. words | Avg. unique words | Avg. Present Symptoms | Avg. Modifiers | Avg. Absent Symptoms | Avg. Negation | Avg. Context-dependent Symptoms |
|---|---|---|---|---|---|---|---|---|
| Dataset | 154 | 2286 | 882 | 8.7 | NA | 8.4 | NA | 1.4 |
| Avg. # words per symptom | | | | 1.7 | 1.3 | 1.5 | 1.0 | 3.0 |
| Avg. # characters of symptoms | | | | 11.2 | 9.9 | 10.3 | 4.2 | 17.5 |
| Top ten frequent symptoms/words | | | | Chest pain | Worsening | Chest pain | No | Weight gain |
| | | | | Pain | increased | Palpitations | denies | Weight loss |
| | | | | Shortness | intermittent | Chills | negative | Decreased appetite |
| | | | | of breath | progressive | Shortness | not | Poor PO intake |
| | | | | Dyspnea | severe | of Breath | resolved | NYHA Class II symptoms |
| | | | | Fatigue | persistent | Abdominal | without | NYHA class III symptoms |
| | | | | Nausea | mild | pain | free | congestive heart failure |
| | | | | Abdominal | improved | Vomiting | less | symptoms |
| | | | | Pain | chronic | Nausea | relief | class IV heart failure |
| | | | | Orthopnea | more | Syncope | never | Ambulated independently |
| | | | | Cough | | Diarrhea | | without difficulty |
| | | | | Syncope | | Cough | | Concentrated urine |

The training set contained 124 notes, with 280,178 total words (Supplemental Table 2-1).

Supplemental Table 2-1. Dataset split.

| Dataset | # reports | # words in total | Present Symptoms | Absent Symptoms | Context-dependent Symptoms |
|---|---|---|---|---|---|
| Train | 124 | 280,178 | 1094 | 1024 | 169 |
| Dev | 15 | 36,512 | 157 | 138 | 35 |
| Test | 15 | 35,467 | 89 | 138 | 17 |
| Total | 154 | 352,157 | 1340 | 1300 | 221 |

Of these, 1,094 (0.4%) were present symptoms, 169 (0.1%) were absent symptoms and 1,024 (0.4%) were context-dependent symptoms. The development set contained 15 notes with 36,512 words, of which 157 (0.4%) were present symptoms, 35 (0.1%) were absent symptoms and 138 (0.4%) were context-dependent symptoms. Finally, the test set contained 15 notes with 35,467 words, of which 89 (0.3%) were present symptoms, 17 (<0.1%) were absent symptoms, and 138 (0.4%) were context-dependent symptoms.

The performance of Graph on the test set is described in Table 2-3.

TABLE 2-3

Results of GraphIE on the test set.

| | Accuracy | Annotated Number of Symptoms | True Positive | False Positive | Precision | Recall | F1 |
|---|---|---|---|---|---|---|---|
| Present | N/A | 89 | 57 | 15 | 79.2% | 64.0% | 70.8 |
| Absent | N/A | 138 | 99 | 27 | 78.6% | 71.2% | 74.7 |
| Context-dependent | N/A | 17 | 7 | 5 | 58.3% | 41.2% | 48.3 |
| Overall | 99.4% | 244 | 163 | 47 | 77.6% | 66.8% | 71.8 |

The algorithm's accuracy was 99.4 and it identified 163/244 symptoms (66.8% recall), among the 35,467 words in the test set. Precision was 77.6%, with 47 words incorrectly tagged as symptoms. The calculated F1 score was 71.8. The algorithm performed better on present (F1 score 70.8) and absent (F1 74.7) symptoms than on context-dependent symptoms (F1 48.3). The ratio of False Positive to True Positive was higher for context-dependent symptoms (0.7), than for present (0.3) and absent (0.3) ones, due to lower precision (58.6%) and recall (41.2%) for the context-dependent category.

The algorithm made several types of errors, which are displayed in Table 7-4.

TABLE 2-4

Typology of errors with examples (Bold text indicates symptom labeling)

| | ANNOTATORS | ALGORITHM |
|---|---|---|
| TYPE 1 | FALSE POSITIVES | |
| | You were admitted to the Brigham and Women's Hospital Cardiology Service for shortness of breath Cardiac: SOB CP, palpitations dependent edema He denied any angina, palpitations. syncope, change in diet or change in medications Patient had repeat evacuation for increasing lethargy and gait instability. Patient demonstrated steady gait with decreased step length on RLE and decreased stance time of LLE with straight LLE gait path | You were admitted to the Brigham and Women's Hospital Cardiology Service for shortness of breath Cardiac: SOB, CP palpitations, dependent edema He denied any angina, palpitations, syncope, change in diet or change in medications Patient had repeat evacuation for increasing lethargy and gait instability. Patient demonstrated steady gait with decreased step length on RLE and decreased stance time of with straight gait path |
| TYPE 2 | PHRASE BOUNDARIES | |
| | Patient is short of breath on mild to moderate exertion. Right sided back pain. Cardiac: SOB, CP, palpitations, dependent edema He presents with episodes of exertional chest pain, associated bilateral arm numbness. | Patient is short of breath on mild to moderate exertion. Right sided back pain. Cardiac: SOB, CP, palpitations, dependent edema He presents with episodes of exertional chest pain, associated bilateral arm numbness. |
| TYPE 3 | INCONSISTENT EXPRESSIONS | |
| | He estimates that he could walk no more than 20-25 feet on flat ground without dyspnea. He notes that his feet might have been cold throughout the summer Patient denies parathesias (sic) Last episode of CP was yesterday evening at 7pm. | He estimates that he could walk no more than 20-25 feet on flat ground ithout dyspnea. He notes that his feet might have been cold throughout the summer Patient denies parathesias (sic) Last episode of CP was yesterday evening at 7pm. |
| TYPE 4 | CATEGORIZATION ERRORS | |
| | Abdominal bloating, loss of appetite (Algorithm: present; Annotators: contextdependent) | Abdominal bloating, loss of appetite (Algorithm: present; Annotators: contextdependent) |

TABLE 2-4-continued

Typology of errors with examples (Bold text indicates symptom labeling)

| ANNOTATORS | ALGORITHM |
|---|---|
| Constitutional: Negative for fever, achills, nd weight loss (Algorithm: absent; Annotators: contextdependent) | Constitutional: Negative for fever, chills, and weight loss (Algorithm: absent; Annotators contextdependent) |

In type 1 errors (False Positives), the algorithm tagged words as symptoms that were not annotated in the gold standard. In most of these errors, a subset of which are illustrated in Supplemental Table 2-2, the system detected words that indicate symptoms (e.g. shortness of breath) but appeared in sections that the annotators ignored (e.g. Patient Instructions). Type 2 errors (Phrase Boundaries) are errors in which the system and the annotators disagreed on the boundaries of the symptom (e.g. whether including the preposition on inside or outside the annotated phrase). Type 3 errors (Inconsistent Expressions) are symptoms with phrasings that were absent from the training set but appear in the test set (e.g. walk no more than 20-25 feet on flat ground). These errors included symptoms with typographical or spelling errors. Type 4 errors are Categorization Errors (e.g. weight loss, which was annotated as context-dependent, but the algorithm tagged as absent).

Supplemental Table 2-2. Partial List of False Positives

| ANNOTATORS | ALGORITHM |
|---|---|
| You were admitted to the <HOSPITAL_NAME> for shortness of breath. | You were admitted to the <HOSPITAL_NAME> for shortness of breath$^{PSY}$. |
| He had increase of left and right sided backs$_{B\text{-}PSY}$ pain (both lateral to the spine). | He had increase of left and right sided back$^{I\text{-}PSY}$ pain (both lateral to the spine). |
| Patient had repeat evacuation in 11/2002 for increasing lethargy and gait instability. | Patient had repeat evacuation in 11/2002 for increasing lethargy$^{PSY}$ and gait instability. |
| Patient had repeat evacuation in 11/2002 for increasing lethargy and gait instability. | Patient had repeat evacuation in 11/2002 for increasing lethargy and gait instability$^{PSY}$. |
| Pt. demonstrated steady gait with decreased step length on RLE and decreased stance time of LLE wit straight gait path. | Pt. demonstrated steady gait with decreased step length on RLE and decreased stance time of LLE wit straight gait path$^{PSY}$. |
| Prior to his admission, the patient had developed dyspnea for a couple of weeks, which was followed by sustained dyspnea with exertion, some orthopnea which was relieved by sitting upright hanging his feet off the bed, and a gradual fluid buildup around his ankles. | Prior to his admission, the patient had developed dyspnea for a couple of weeks, which was followed by sustained dyspnea with exertion, some orthopnea which was relieved by sitting upright hanging his feet off the bed$^{PSY}$, and a gradual fluid buildup around his ankles. |
| 61-year-old male with history of hypertension CHF ischemic rmj cardiomyopathy pacemaker with AICD depression sleep apnea question COPD presents with one-week history of shortness of breath and generalized$_{PSY}$ weakness$_{PSY}$. | 61-year-old male with history of hypertension CHF ischemic rmj cardiomyopathy pacemaker with AICD depression sleep apnea question COPD presents with one-week history of shortness of breath and generalized weakness$^{PSY}$. |
| Over the past 2 days, his edema has worsened into his upper thighs and scrotum | Over the past 2 days, his edema has worsened into his upper thighs$^{PSY}$ and scrotum |
| He has been dyspneic$^{PSY}$ with walking just a few steps, prompting him to come to the ED today. | He has been dyspneic with walking just a few steps$^{PSY}$, prompting him to come to the ED today. |
| Patient is short of breath on$_{B\text{-}PSY}$ mild to moderate exertion, which impacts the quality of his life but he is able to do most of his day-to-day things without significant limitations. | Patient is short of breath on$^{I\text{-}PSY}$ mild to moderate exertion, which impacts the quality of his life but he is able to do most of his day-to-day things without significant limitations. |
| Patient describes pain as sharp and brief "like a knife stab" on Thursday night which was brief (a few seconds). | Patient describes pain as sharp$^{PSY}$ and brief "like a knife stab" on Thursday night which was brief (a few seconds). |
| Lidoderm patch was ordered for pain relief though pain$_{NSY}$ resolved spontaneously without need to use patch and remained pain free throughout the time on the floor. | Lidoderm patch was ordered for pain relief though pain$^{PSY}$ resolved spontaneously without need to use patch and remained pain free throughout the time on the floor. |
| Lidoderm patch was ordered for pain relief though pain resolved spontaneously without | Lidoderm patch was ordered for pain relief though pain resolved spontaneously |

Supplemental Table 2-2. Partial List of False Positives

| ANNOTATORS | ALGORITHM |
|---|---|
| need to use patch and remained pain$_{NSY}$ free throughout the time on the floor. | without need to use patch and remained pain$^{PSY}$ free throughout the time on the floor. |
| Prior to his admission, the patient had developed dyspnea for a couple of weeks, which was followed by sustained dyspnea with exertion, some orthopnea which was relieved by sitting upright hanging his feet off the bed, and a gradual fluid buildup around his ankles. | Prior to his admission, the patient had developed dyspnea for a couple of weeks, which was followed by sustained dyspnea with exertion, some orthopnea which was relieved by sitting upright hanging his feet off the bed$^{PSY}$, and a gradual fluid buildup around his ankles. |
| Patient denies parathesias. | Patient denies parathesias$^{NSY}$. |
| Back: Negative for injury and pain | Back: Negative for injury$^{NSY}$ and pain |
| GU: Negative for dysuria frequency$_{B-NSY}$ urgency or hematuria | GU: Negative for dysuria frequency$^{I-NSY}$ urgency or hematuria |
| MS/Extremity: Negative for injury and deformity | MS/Extremity: Negative for injury$^{NSY}$ and deformity |
| MS/Extremity: Negative for injury and deformity | MS/Extremity: Negative for injury and deformity$^{NSY}$ |
| Skin: Negative for injury, rash, and discoloration | Skin: Negative for injury$^{NSY}$, rash, and discoloration |
| Neuro: Negative for headache, weakness, numbness, tingling, and seizure. | Neuro$^{NSY}$: Negative for headache, weakness, numbness, tingling, and seizure. |

$^{PSY}$: Positive symptom;
$^{NSY}$: Negative symptom;
NEU: Context-dependent symptom As used herein, the terms comprise, include, and/or plural forms of each are open ended and include the listed parts and can include additional parts that are not listed. The term and/or is open ended and includes one or more of the listed parts and combinations of the listed parts.

As used herein, the term "therapeutic substance" means any tangible chemical, drug, medicine or pharmacological substance, either synthetic or naturally occurring, regardless of the form of administration to the subject, that is administered to the body of the subject.

At various places in the present specification, values are disclosed in groups or in ranges. It is specifically intended that the description include each and every individual sub-combination of the members of such groups and ranges and any combination of the various endpoints of such groups or ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto. For example, though free-written text was used as a proof-of-concept, these methods are not limited to purely text-based data and can be expanded to utilize other data sources.

What is claimed is:

1. A method for identifying a symptom in text data comprising:
   A) processing a plurality of free-running text into a segmented text data set;
   B) labeling words in the segmented text data set, including one or more symptom terms each associated with a specific symptom and associating a tag and a position with a labeled word, the tag indicating any of a positive, negative, or neutral value relative to the symptom term, wherein a positive value indicates a presence of a symptom term and wherein a negative value indicates an absence of a symptom term and wherein a neutral value indicates no relationship to a symptom term;
   C) processing, with the natural language processing algorithm, a first subset of the text data set containing labeled symptom terms; and
   D) processing, with the natural language processing algorithm, a second subset of the text data set containing labeled symptom terms.

2. The method of claim 1 further comprising:
   E) processing, with the natural language processing algorithm, a third subset of the text data containing labeled symptom terms.

3. The method of claim 1 further comprising:
   E) following D), processing, with the natural language processing algorithm, another text data set not containing labeled symptom terms.

4. The method of claim 3 further comprising:
   E) correlating a frequency of a labeled symptom term having a tag indicating a positive status with any of a pathology, therapeutic substance, therapeutic procedure, or therapeutic device.

5. The method of claim 1 wherein B) comprises:
   B1) labeling another term in a same segment of the text data set as an attribute of a labeled symptom term, if the another term describes any of a negation, frequency, severity, change or interference with a symptom identified by the labeled symptom term.

6. The method of claim 5 wherein the other correlation status with the symptom term is context-dependent status.

7. The method of claim 1 wherein the other correlation status with the symptom term is a neutral status.

8. The method of claim 1 wherein a symptom term or another term comprises any of a single word, multiple words, number, acronym, graphic element or any combination thereof.

9. The method of claim 1 wherein the plurality of symptom terms are associated with any of a pathology, therapeutic substance, therapeutic procedure, or therapeutic device.

10. The method of claim 1 wherein C) comprises processing the first subset of the text data with any of a Conditional Random Field Model process.

11. The method of claim 1 wherein D) comprises processing the first subset of the text data with a Conditional Random Field Model process.

12. A method for identifying a symptom in text data comprising:
   A) defining a plurality of symptom terms;
   B) selecting a text data set including at least a subset of the plurality of defined symptom terms;
   C) labeling, in the text data set, defined symptom terms and associating a position of the labeled symptom term within the text data set and further associating a tag indicating any of a positive, negative, or neutral value relative to the labeled symptom term, wherein a positive value indicates a presence of a symptom term and wherein a negative value indicates an absence of a symptom term and wherein a neutral value indicates no relationship to a symptom term;
   D) processing, with multiple natural language processing algorithms, a first subset of the text data set containing labeled symptom terms to identify a frequency of occurrences of a symptom term in the first subset of the text data;
   E) scoring accuracy of the multiple natural language processing algorithms in processing the first subset of the text data; and
   F) processing, with a natural language processing algorithm having greatest accuracy in step E), a second subset of the text data set containing labeled symptom terms.

13. The method of claim 12 further comprising:
   G) processing, with the natural language processing algorithm, a third subset of the text data containing labeled symptom terms.

14. The method of claim 12 further comprising:
   G) following F), processing, with the natural language processing algorithm, another text data set not containing labeled symptom terms.

15. The method of claim 14 further comprising:
   G) correlating a frequency of a labeled symptom term having a tag indicating a positive status with any of a pathology, therapeutic substance, therapeutic procedure, or therapeutic device.

16. The method of claim 12 wherein C) comprises:
   C1) labeling another term in the text data set as an attribute of a labeled symptom term, if the another term describes any of a negation, frequency, severity, change or interference with a symptom identified by the labeled symptom term.

17. The method of claim 16 wherein the other correlation status with the symptom term is context-dependent status.

18. The method of claim 12 wherein the other status with the symptom term is a neutral status.

19. The method of claim 12 wherein one of the symptom term or another term comprises any of a single word, multiple words, number, acronym, graphic element or any combination thereof.

20. The method of claim 12 wherein the plurality of symptom terms are associated with any of a pathology, therapeutic substance, therapeutic procedure, or therapeutic device.

* * * * *

UNITED STATES PATENT AND TRADEMARK OFFICE
CERTIFICATE OF CORRECTION

PATENT NO. : 11,915,828 B2
APPLICATION NO. : 16/891305
DATED : February 27, 2024
INVENTOR(S) : Charlotta Lindvall It is certified that error appears in the above-identified patent and that said Letters Patent is hereby corrected as shown below:

In the Claims

Column 26, Lines 60-64, please delete Claim 4, as follows:
"4. The method of claim 3 further comprising:
    E) correlating a frequency of a labeled symptom term having a tag indicating a positive status with any of a pathology, therapeutic substance, therapeutic procedure, or therapeutic device."

Replace with:
--4. The method of claim 3 further comprising:
    F) correlating a frequency of a labeled symptom term having a tag indicating a positive status with any of a pathology, therapeutic substance, therapeutic procedure, or therapeutic device.--

Column 28, Lines 16-20, please delete Claim 15, as follows:
"15. The method of claim 14 further comprising:
    G) correlating a frequency of a labeled symptom term having a tag indicating a positive status with any of a pathology, therapeutic substance, therapeutic procedure, or therapeutic device."

Replace with:
--15. The method of claim 14 further comprising:
    H) correlating a frequency of a labeled symptom term having a tag indicating a positive status with any of a pathology, therapeutic substance, therapeutic procedure, or therapeutic device.--

Signed and Sealed this
Third Day of September, 2024

Katherine Kelly Vidal
*Director of the United States Patent and Trademark Office*